US00PP32107P3

(12) United States Plant Patent
van Heesbeen

(10) Patent No.: US PP32,107 P3
(45) Date of Patent: Aug. 18, 2020

(54) *STOKESIA* PLANT NAMED 'MEGA MELS'

(50) Latin Name: *Stokesia laevis*
Varietal Denomination: Mega Mels

(71) Applicant: Van Heesbeen Cultures B.V., Rijsbergen (NL)

(72) Inventor: Ad van Heesbeen, Rijsbergen (NL)

(73) Assignee: Van Heesbeen Cultures B.V., Rijsbergen (NL)

( * ) Notice: Subject to any disclaimer, the term of this patent is extended or adjusted under 35 U.S.C. 154(b) by 0 days.

(21) Appl. No.: 16/501,670

(22) Filed: May 20, 2019

(65) Prior Publication Data

US 2019/0357414 P1 Nov. 21, 2019

(30) Foreign Application Priority Data

May 18, 2018 (QZ) ..... PBR 2018/1335

(51) Int. Cl.
*A01H 5/02* (2018.01)
*A01H 6/14* (2018.01)

(52) U.S. Cl.
USPC ..... Plt./484
CPC ..... *A01H 6/14* (2018.05)

(58) Field of Classification Search
USPC ..... Plt./484
See application file for complete search history.

(56) References Cited

U.S. PATENT DOCUMENTS

PP10,660 P * 10/1998 Warren ..... Plt./484

* cited by examiner

*Primary Examiner* — Susan McCormick Ewoldt
(74) *Attorney, Agent, or Firm* — Samuel R. McCoy, Jr.

(57) ABSTRACT

A new and distinct *Stokesia* plant named 'Mega Mels' which is characterized by the combination of a large plant size, globular habit, large light purple flowers with yellow centers, and the stability of these characteristics from generation to generation.

2 Drawing Sheets

Latin name of the genus and species: The Latin name of the genus and species of the novel variety disclosed herein is *Stokesia laevis*.

Variety denomination: The inventive cultivar of *Stokesia* disclosed herein has been given the variety denomination 'Mega Mels'.

CROSS REFERENCE TO RELATED APPLICATIONS

This application claims priority to the Community Plant Variety Rights application number 2018/1335, filed May 18, 2018, which is herein incorporated by reference.

BACKGROUND OF THE INVENTION

Parentage: 'Mega Mels' is a seedling selection resulting from the controlled pollination of the seed parent, *Stokesia laevis* 'Mels Blue' (U.S. Plant Pat. No. 23,090), with an unnamed *Stokesia laevis* plant (not patented), the pollen parent. The crossing was made by the inventor in April of 2014 at a commercial greenhouse in Rijsbergen, the Netherlands. In August of 2015, one seedling from said cross was observed which exhibited large, light purple flowers. The seedling was isolated for further evaluation in order to confirm the distinctness and stability of the characteristics first observed. Upon confirmation of distinctness and stability, 'Mega Mels' was selected for commercialization.

Asexual Reproduction: Asexual reproduction of 'Mega Mels', by way of softwood stem cuttings, was first performed in August of 2015 in Rijsbergen, the Netherlands.

Through five subsequent generations, the unique features of this cultivar have proven to be stable and true to type.

SUMMARY OF THE INVENTION

The cultivar 'Mega Mels' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Mega Mels'. These characteristics in combination distinguish 'Mega Mels' as a new and distinct *Stokesia laevis* cultivar:

1. *Stokesia* 'Mega Mels' exhibits a relatively large plant size; and
2. *Stokesia* 'Mega Mels' exhibits a globular plant shape; and
3. *Stokesia* 'Mega Mels' exhibits large, light purple flowers which are conspicuously centered yellow.

BOTANICAL DESCRIPTION OF THE PLANT

Figure 1:
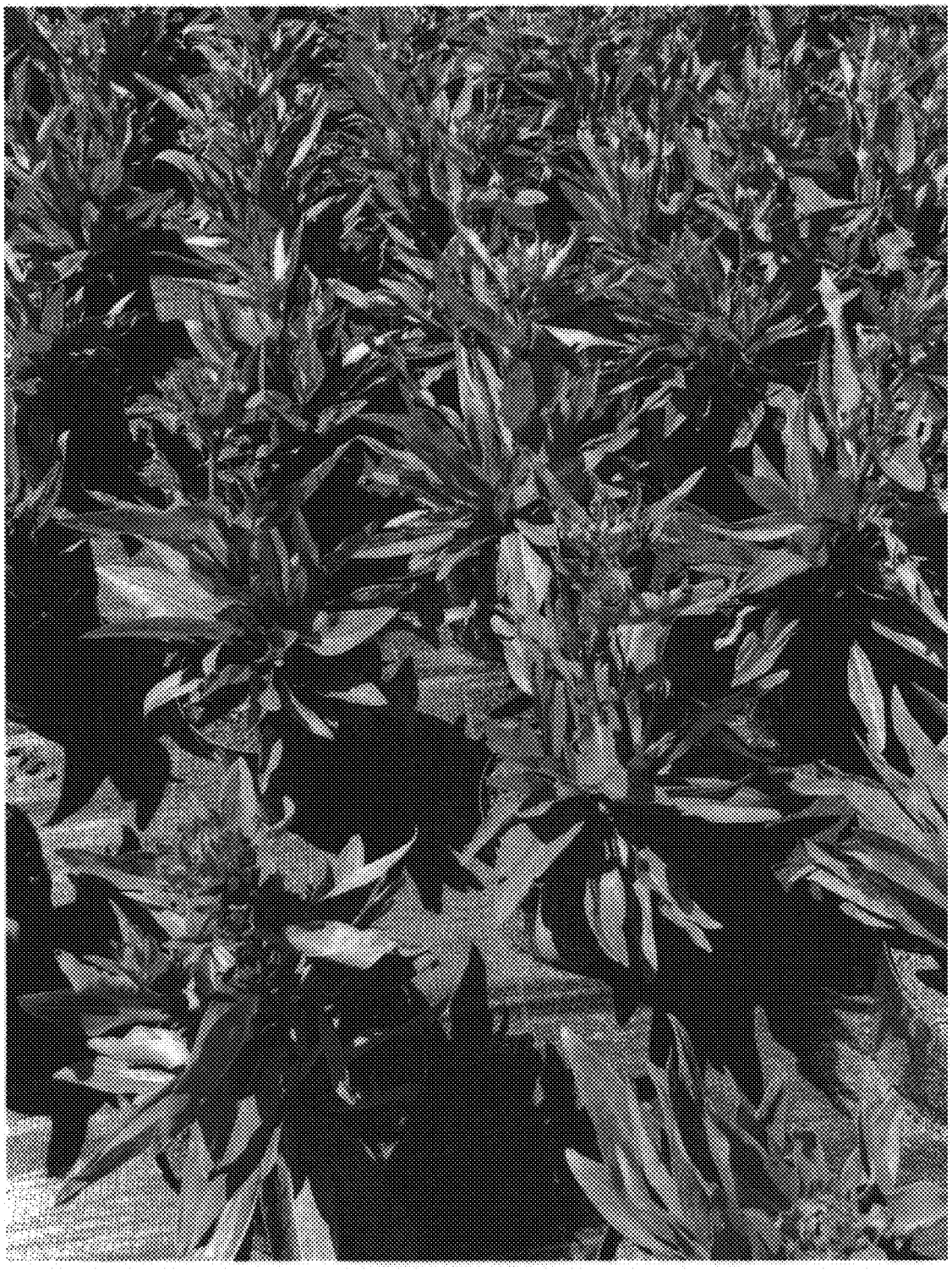
FIG. 1 illustrates, as nearly true as it is reasonably possible to make the same in color photographs of this type, exemplary saleable 'Mega Mels' plants, at 5 months of age, grown outdoors in 140 mm nursery containers at the inventor's commercial greenhouse in Rijsbergen, the Netherlands.
Figure 2:
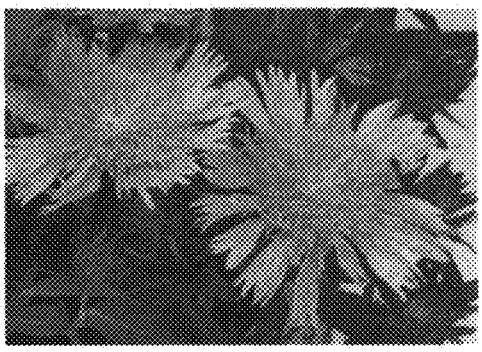
FIG. 2 illustrates, as nearly true as it is reasonably possible to make the same in color photographs of this type, the typical flowers of 'Mega Mels'.

The following observations and measurements, made in September of 2019, describe averages from a sample set of six specimens of one year old 'Mega Mels' plants grown in 17 cm nursery containers in Rijsbergen, the Netherlands. Plants were produced outdoors with full sun exposure and maintained using overhead irrigation at regular intervals, and were fertilized as required using a slow release fertilizer. No chemical pest control measures were utilized during production.

Those skilled in the art will appreciate that certain characteristics will vary with older or, conversely, with younger plants. 'Mega Mels' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 edition.

A botanical description of 'Mega Mels' and comparisons with the parents and most similar variety of common knowledge are provided below.

General plant description:

*Growth habit*.—A broad, upright herbaceous perennial with inflorescence carried within and above the foliage.

*Plant profile*.—Obovate.

*Height*.—30.5 cm to the top of the foliar plane; 34.4 cm to the top of the floral plane.

*Spread*.—30.0 cm.

*Plant vigor*.—Moderately vigorous.

*Growth rate*.—Moderately fast growing.

*Propagation*.—Method — Softwood stem cuttings. Time to initiate rooting — Rooting is initiated in approximately 14 days when grown in a greenhouse with an ambient average temperature of 15 degrees Celsius. Time to produce a finished plant — Approximately 12 weeks are required to produce a marketable finished plant in an 11 cm pot.

*Pest resistance and susceptibility*.—Not any more or less tolerant or susceptible to pests or diseases known to effect *Stokesia*.

*Environmental tolerances*.—Cold hardy to USDA Hardiness Zone 6 and temperatures as high as 35 degrees Celsius; drought tolerant once established.

Root system:

*General*.—Moderately freely branched and moderately dense rooting.

*Distribution in the soil profile*.—Shallow to moderately deep.

*Texture*.—Non-fibrous, non-fleshy.

*Color*.—Yellow-white, nearest to a mixture of RHS 158C and 158D.

Stem:

*Branching habit*.—Basally branching main stem; freely branching with lateral branches.

*Number of main stems per plant*.—8.

*Number of lateral branches per main stem*.—1.

*Aspect of main stems and lateral branches*.—Rounded.

*Lateral branch length*.—18.9 cm.

*Lateral branch diameter*.—0.55 cm.

*Internode length*.—4.5 cm.

*Attitude*.—Main stems are an average angle of 10 degrees from vertical; stems vary from between 0 to 20 degrees from vertical. Lateral branches are at an average angle of 20 degrees to the main stems.

*Strength*.—Moderately strong.

*Pubescence*.—Densely covered with short, sericeous hairs with an average length of 0.2 cm and colored greyed-white, nearest to RHS 157D.

*Luster*.—Matte.

*Color, juvenile*.—Yellow-green, nearest RHS 145A.

*Color, mature*.—Yellow-green, nearest to in between RHS 146C and 146D, and becoming progressively darker with age, RHS 148A.

*Color at internodes*.—Yellow-green, nearest to in between RHS 146C and 146D, and becoming progressively darker with age, RHS 148A.

Foliage:

*General*.—Leaves are borne both basally and on stems.

*Basal leaves*.—Arrangement — Alternate. Attachment — Sessile. Division — Simple. Shape — Lanceolate. Dimensions — 18.9 cm long, including petiole, and 3.4 cm wide. Attitude — Outward and upward. Apex — Acute to bluntly acute. Base — Long acuminate; decurrent. Margins — Entire; very slightly undulate. Texture and luster, adaxial and abaxial surfaces — Smooth, glabrous, and matte. Luster, adaxial and abaxial surfaces — Very slightly glossy. Color — Juvenile foliage color, adaxial surface — Yellow-green, nearest to RHS 144A. Juvenile foliage color, abaxial surface — Yellow-green, nearest to in between RHS 143A and 144A. Mature leaf color, adaxial surface — Green, nearest to in between RHS NN137A and NN137B. Mature leaf color, abaxial surface — Yellow-green, nearest to RHS 146B. Venation — Type — Pinnate. Vein color, adaxial surface — Yellow-green, nearest to a mixture of RHS 145B and 145C. Vein color, abaxial surface — Yellow-green, nearest to a mixture of RHS 145A and 145B. Petiole — None present; leaves are sessile. Stipules — None present.

*Cauline leaves*.—Arrangement — Alternate. Attachment — Sessile. Division — Simple. Shape — Lanceolate. Dimensions — 12.7 cm long, including petiole, and 3.3 cm wide. Attitude — Outward and upward. Apex — Acute to bluntly acute. Base — Long acuminate; decurrent. Margins — Entire, occasionally with one to three teeth present near the leaf base; very slightly undulate. Texture and luster, adaxial and abaxial surfaces — Smooth, glabrous, and matte. Luster, adaxial and abaxial surfaces — Very slightly glossy. Color — Juvenile foliage color, adaxial surface — Yellow-green, nearest to RHS 144A. Juvenile foliage color, abaxial surface — Yellow-green, nearest to in between RHS 143A and 144A. Mature leaf color, adaxial surface — Green, nearest to in between RHS NN137A and NN137B. Mature leaf color, abaxial surface — Yellow-green, nearest to RHS 146B. Venation — Type — Pinnate. Vein color, adaxial surface — Yellow-green, nearest to a mixture of RHS 145B and 145C. Vein color, abaxial surface — Yellow-green, nearest to a mixture of RHS 145A and 145B. Petiole — None present; leaves are sessile. Stipules — None present.

Inflorescence:

*Type*.—Terminal capitula comprised of a receptacle, disc florets, and ray florets.

*Natural flowering season*.—Summer into autumn in Rijsbergen, the Netherlands.

*Flowering habit*.—Very freely flowering.

*Dimensions*.—3.5 cm high, not including peduncle, and 13.0 cm in diameter.

*Quantity of inflorescence per plant*.—32, on average; typically 4 per lateral branch.

*Attitude*.—Upright.

*Peduncles*.—Length — Primary peduncles are 4.8 cm long on average; lateral peduncles are 3.4 cm on average. Diameter — Primary peduncles are 0.35 cm in diameter, on average; lateral peduncles are 0.25 cm on average. Attitude — Primary peduncles are upright; lateral peduncles are at an angle of 20 degrees to the primary peduncles. Strength — Strong. Texture — Densely pubescent; short, sericeous hairs with an average length of 0.2 cm and colored green-white, RHS 157D. Luster — Matte. Color — Yellow-green, nearest to a mixture of RHS 145A and 145B.

Flower buds:

*Shape*.—Spherical.

*Length*.—Average of 2.8 cm.

*Diameter*.—Average of 1.7 cm.

*Texture*.—Smooth; glabrous.

*Luster*.—Matte.

*Color*.—Greyed-yellow, nearest to a mixture of RHS 161B and 161C.

Flower:

*Flower type*.—Composite; capitula.

*Fragrance*.—None.

*Flower longevity*.—10 days, on average.

*Persistence*.—Persistent.

*Disc diameter*.—5.0 cm.

*Receptacle shape*.—Flattened.

*Receptacle height*.—0.4 cm.

*Receptacle diameter*.—1.3 cm.

*Receptacle color*.—Yellow-green, nearest to RHS 138C.

*Ray florets*.—Quantity of florets per capitula — 20. Shape — Oblanceolate; proximal 25 percent of the floret is tubular. Arrangement — Rotate with a single whorl of florets around disc; florets are unfused. Attitude — Outward, with an average angle of 10 degrees to horizontal. Aspect — Carinate. Dimensions — 6.6 cm long and 2.0 cm wide. Apex — Lanciniate. Base — Long, narrow cuneate. Margin — Entire; not undulated. Texture and luster, upper surface — Glabrous, moderately velvety and slightly glossy. Texture and luster, lower surface — Glabrous, moderately velvety and slightly glossy. Color, when opening, upper surface — Violet, nearest to N88C. Color, when opening, lower surface — Violet, nearest to in between N87C and N87D; basal tube is nearest to RHS N87C. Color, when fully opened, upper surface — Violet, nearest to N88C. Color, when fully opened, lower surface — Violet, nearest to N88C. Venation, when fully opened, upper surface — Violet, nearest to RHS N88C; basal tube is nearest to RHS N87B. Venation, when fully opened, lower surface — Violet, nearest to RHS N88C; basal tube is nearest to RHS N87B.

*Disc florets*.—Quantity of florets per capitula — 130. Arrangement — Radial symmetry; five whorls of florets. Shape — Tubular; proximal 50 percent of florets are fused, typically with 5 free apical lobes. Attitude — Upright and outward; at an average angle of 20 degrees to horizontal. Length — 3.0 cm. Width — 1.5 cm. Apex of the floret lobe — Lanciniate; apical lobes are narrowly acute. Base — Fused into a tube. Margin of the free floret lobe — Entire; not undulated. Texture and luster, upper surface — Smooth, glabrous and slightly glossy. Texture and luster, lower surface — Smooth, glabrous and slightly glossy. Color, when opening, upper surface — Violet, nearest to RHS N87C; mid-section is slightly darker, nearest to RHS N87B; base is green-white, nearest to RHS 157C. Color, when opening, lower surface — Violet, nearest to RHS N87C; mid-section is slightly darker, nearest to RHS N87B; base is green-white, nearest to RHS 157C. Color, when fully opened, upper surface — Violet, nearest to a mixture of RHS N87C and N87D; mid-section is slightly darker, nearest to a mixture of RHS N87B and N87C; base is green-white, nearest to a mixture of RHS 157C and 157D. Color, when fully opened, lower surface — Violet, nearest to a mixture of RHS N87C and N87D; mid-section is slightly darker, nearest to a mixture of RHS N87B and N87C; base is green-white, nearest to a mixture of RHS 157C and 157D. Faded color, upper surface — Not fading. Faded color, lower surface — Not fading. Venation, upper and lower surfaces — No visible venation. Disc floret bracts — Quantity — One bract is present at the base of each disc floret. Arrangement — Rotate. Length — 1.0 cm. Diameter — 0.5 cm. Shape — Linear. Apex — Narrowly acute. Base — Cuneate. Margin — Entire. Texture and luster — Smooth, glabrous, and glossy. Color — White, nearest to RHS NN155A.

*Involucre; phyllaries*.—Arrangement — Rotate; free; five whorls around the disc with the upper whorl exhibiting unique morphological characteristics relative to the lower four whorls. Quantity — 60. Upper whorl of phyllaries — Length — 1.4 cm. Width — 0.2 cm. Shape — Narrow oblong. Apex — Obtuse. Base — Cuneate. Margin — Entire. Texture and luster, upper surface — Glabrous; glossy. Texture and luster, lower surface — Glabrous; glossy. Color, fully opened, upper surface — Yellow-green, nearest to RHS 145C; apex is greyed-yellow, nearest to RHS 161C. Color, fully opened, lower surface — Yellow-green, nearest to RHS 145C; apex is greyed-yellow, nearest to RHS 161C. Lower whorls of phyllaries — Length — 1.7 cm. Width — 1.1 cm. Shape — Ovate to elliptic. Apex — Mucronate. Base — Cuneate. Margin — Coarsely dentate with mucronate teeth. Texture and luster, upper surface — Glabrous; matte. Texture and luster, lower surface — Glabrous; matte. Color, fully opened, upper surface — Green, nearest to RHS 137B. Color, fully opened, lower surface — Green, nearest to RHS 137D.

Reproductive organs:

*Androecium*.—Stamens — Quantity — 5 per disc floret; none present on ray florets. Anthers — Shape — Narrow oblong. Dimensions — Approximately 0.5 cm long and 0.5 cm wide. Color — White, nearest to RHS 155A. Filaments — Length — 1.2 cm. Color — White, nearest to RHS NN155D. Pollen, amount — Moderately abundant to abundant. Pollen color — Green-white, nearest to RHS 157C.

*Gynoecium*.—Pistil — Quantity — 1 pistil for each disc floret; no pistils present on ray florets. Length — 2.3 cm. Style — Length — 2.1 cm. Color — White, nearest to RHS NN155D. Stigma — Shape — Cleft; decurrent. Diameter — 0.8 cm. Color — White, nearest to RHS NN155B. Ovary Color — White, RHS 155C.

Seed and fruit: Botanical description is not yet available.

COMPARISONS WITH THE PARENTS

Plants of the new cultivar 'Mega Mels' differ from its parent, *Stokesia laevis* 'Mels Blue' (U.S. Plant Pat. No. 23,090), by the characteristics described in Table 1.

TABLE 1

| Characteristic | 'Mega Mels' | 'Mels Blue' |
|---|---|---|
| Plant height. | Taller than 'Mels Blue'. | Shorter than 'Mega Mels'. |
| General coloration of the flower. | Light purple and lightly suffused with pink, Flowers are conspicuously centered yellow. | Dark purple. Flowers are inconspicuously centered yellow. |

Plants of the new cultivar 'Mega Mels' differ from its pollen parent, an unnamed *Stokesia laevis* plant (not patented), by the characteristics described in Chart 2.

CHART 2

| Characteristic | 'Mega Mels' | The pollen parent |
|---|---|---|
| Abundance of foliage. | More abundant. | Less abundant. |
| Foliage thickness. | Thicker than the pollen parent. | Thinner than 'Mega Mels'. |

CHART 2-continued

| Characteristic | 'Mega Mels' | The pollen parent |
|---|---|---|
| General coloration of mature foliage. | Lighter green. | Darker green. |
| Floriferousness. | More flowers per plant. | Fewer flowers per plant. |
| Abundance of involucral bracts. | More abundant. | Less abundant. |

COMPARISONS WITH THE MOST SIMILAR VARIETY OF COMMON KNOWLEDGE

Plants of the new cultivar 'Mega Mels' may be distinguished from the variety *Stokesia laevis* 'Mini Mels' (U.S. patent application Ser. No. 16/501,668) by the combination of characteristics described in Table 2.

TABLE 2

| Characteristic | 'Mega Mels' | 'Mini Mels' |
|---|---|---|
| Floriferousness. | Fewer flowers per plant. | More flowers per plant. |
| Flower size. | Larger than 'Mini Mels'. | Smaller than 'Mega Mels'. |
| Abundance of involucral bracts. | More abundant. | Less abundant. |
| Attitude of involucral bracts. | More relaxed. | More upright. |
| General coloration of the flower. | Light purple and lightly suffused with pink; inconspicuously centered yellow. | Dark purple; conspicuously centered lighter yellow. |

That which is claimed is:

1. A new and distinct cultivar of *Stokesia* plant named 'Mega Mels', substantially as described and illustrated herein.

* * * * *